United States Patent
D'Alché-Birée

(12) 
(10) Patent No.: US 6,534,500 B2
(45) Date of Patent: Mar. 18, 2003

(54) USE OF CYAMEMAZINE IN THE TREATMENT OF ABRUPT BENZODIAZEPHINE WITHDRAWAL

(75) Inventor: Francoise D'Alché-Birée, Paris (FR)

(73) Assignee: Aventis Pharma S.A.

( * ) Notice: Subject to any disclaimer, the term of this patent is extended or adjusted under 35 U.S.C. 154(b) by 0 days.

(21) Appl. No.: 10/073,436

(22) Filed: Feb. 11, 2002

(65) Prior Publication Data
US 2002/0183332 A1 Dec. 5, 2002

Related U.S. Application Data

(63) Continuation of application No. PCT/FR00/02186, filed on Jul. 28, 2000.

(30) Foreign Application Priority Data

Aug. 13, 1999 (FR) .............................................. 99 10472

(51) Int. Cl.⁷ .............................................. A61K 31/54
(52) U.S. Cl. .................................................. 514/226.2
(58) Field of Search ....................................... 514/226.2

(56) References Cited

U.S. PATENT DOCUMENTS 2,877,224 A * 3/1959 Jacob et al. ................. 260/243
4,666,903 A * 5/1987 Gallager ...................... 514/220
5,162,323 A   11/1992 Pares-Constansa
5,470,868 A * 11/1995 Young ......................... 514/397

FOREIGN PATENT DOCUMENTS

EP        98/43656        10/1998

OTHER PUBLICATIONS

Naassila, Michael et al., Cyamemazine Decreases Ethanol Intake In Rats and Convulsions During Ethanol Withdrawal Syndrome In Mice, Psychopharmacology (1998), vol. 140, pp. 421–428.

Parquet, P. J., Drugs Used in the Treatment of Psychoactive Substances Withdrawal, Les Medicaments DU Sevrage Des Toxicomanies, vol. 21–13, pp. 2012–2016 (1989).

Reynolds, E.F., Cyamemazine, Martindale (Thirty First Edition 1996, vol. 3, p. 699).

* cited by examiner

Primary Examiner—Raymond Henley, III
(74) Attorney, Agent, or Firm—James W. Bolcsak

(57) ABSTRACT

The present invention relates to the use of cyamamazine, or the pharmaceutically acceptable salts thereof, in the treatment of abrupt benzodiazepine withdrawal.

4 Claims, No Drawings

USE OF CYAMEMAZINE IN THE TREATMENT OF ABRUPT BENZODIAZEPHINE WITHDRAWAL

This application is a continuation of PCT/FR/00/02186 filed Jul. 28, 2000.

The present invention relates to the use of cyamemazine, or the pharmaceutically acceptable salts thereof, in the treatment of abrupt benzodiazepine withdrawal by substitution of the benzodiazepine with cyamemazine.

Benzodiazepines, such as bromazepam, oxazepam, lorazepam, alprozolam, diazepam, prazepam, nordazepam, clobazam, clotiazepam or aprazolam, are the reference medicinal treatment for anxious disorders. However, the occurrence of psychological and/or physical dependency has been described in prescriptions for greater than 6 weeks (KG. POWER et al., Br. Med. J., 290, 1246 (1985)). The frequency of occurrence of the withdrawal syndrome after benzodiazepine has been stopped varies depending on the criteria chosen, but is generally of the order of 40% (R. NOYES et al., J. Clin. Psychiatry, 49, 382 (1988)).

It is therefore recommended, firstly, to limit the prescription of benzodiazepines to 3 months, renewable in certain cases of severe anxiety, and, secondly, to stop the treatment gradually. However, even when the treatment is stopped gradually, the occurrence of a withdrawal symptom may be noted, which is responsible for the benzodiazepine treatment being recommenced (E. SCHWEIZER et al., Arch. Gen. Psychiatry, 47, 908 (1990)).

Cyamemazine (TERCIAN$^{(R)}$) is a sedative neuroleptic which, at low dose, is well tolerated. It is a treatment for anxiety which is indicated when the usual therapeutics are ineffective or in cases of neurotic or psychotic anxieties. It is also known for its action on the decrease of alcohol uptake in rats (N. NAASILA et al., Psychopharmacology, 140, 421 (1998)).

Non-benzodiazepine anxiolytics, such as buspirone, have been tested in benzodiazepine withdrawal, but have not shown any significant effect on the withdrawal syndrome (LADER et al., Journal of Clinical Psychopharmacology, 7, 1 (1987); SCHWEIZER et al., Acta Psychiatr Scandinavia, 98, sup 393 (1998)).

It has now been found that cyamemazine makes it possible to treat the symptoms, and in particular the anxiety rebound and withdrawal syndrome, occurring when benzodiazepine treatment is stopped, and thus to avoid the taking of benzodiazepines being recommenced and the treatment being perpetuated. This effect is always noted 6 months after treatment.

During a clinical trial, 2 strategies for stopping benzodiazepines were compared: either gradual withdrawal with a benzodiazepine (bromazepam) or abrupt withdrawal and substitution with cyamemazine.

The cyamemazine was studied in 168 patients, 18 to 65 years old, who had been treated with benzodiazepines (bromazepam, oxazepam, lorazepam or alprazolam) for 3 months or more, at a dose greater than or equal to 5 mg diazepam equivalent and less than 20 mg diazepam equivalent for at least 15 days, and who exhibited a score on the HAMILTON anxiety scale (Br. J. Med. Psychol., 32, 50 (1959)) of less than 18 and required benzodiazepine withdrawal. Diazepam equivalence table:

| PRODUCTS | DOSE (mg) |
| --- | --- |
| diazepam | 10 |
| alprazolam | 1 |
| bromazepam | 6 |
| lorazepam | 2.5 |
| oxazepam | 50 |

This is a randomized double-blind treatment which occurs over 3 periods:

1—Substitution period

The benzodiazepine is replaced either with cyamemazine or with bromazepam.

The dose is set according to the prior benzodiazepine treatment:

it is 4 gelatin capsules, taken as 2 or 3 doses a day, containing a dose of 12.5 mg of cyamemazine or 1.5 mg of bromazepam, when the prior dose of benzodiazepine is equal to or greater than 10 mg diazepam equivalents and less than 20 mg diazepam equivalent, it is 2 gelatin capsules, taken as 2 doses a day, containing a dose of 12.5 mg of cyamemazine or 1.5 mg of bromazepam when the prior dose of benzodiazepine is equal to or greater than 5 mg diazepam equivalent and less than 10 mg diazepam equivalent.

2—Dose reduction period

The dose is either 1 or 2 gelatin capsules at 12.5 mg of cyamemazine or at 1.5 mg of bromazepam a day for 14 days, or 1 or 2 gelatin capsules at 12.5 mg of cyamemazine or at 1.5 mg of bromazepam a day for 11 days, and then 3 days of placebo.

3—Stopping period 1 or 2 gelatin capsules of placebo a day for 14 days.

The results are determined for each patient according to the following criteria:

HAMILTON anxiety scale (HARS)

ZUNG anxiety self-assessment (Official Journal of the Academy of Psychosomatic Medicine, Vol XII, No. 6 (1971))

RICKELS withdrawal scale (Arch. Gen. Psychiatry, Vol 47 (1990))

The results obtained in each of these tests make it possible to deduce that there is no significant difference between the cyamemazine treatment group and the bromazepam treatment group, concerning the maximum amplitude of the anxiety rebound (HARS scale and ZUNG anxiety scale) and the percentage of patients exhibiting an anxiety rebound. The RICKELS withdrawal scale also shows no significant difference between the 2 treatment groups concerning the frequency of occurrence of a withdrawal syndrome. However, after 6 weeks of study, the treatment is successful in a greater number of patients from the cyamemazine group (95%) than patients from the bromazepam group (85%). Moreover, after a considerable period of time (6 months) the withdrawal is still a success in 90% of the patients on cyamemazine versus 75% on bromazepam.

These results demonstrate that, when it is necessary to stop a chronic benzodiazepine treatment, cyamemazine may be used through abrupt substitution for the benzodiazepine without any consequences linked to the occurrence of an anxiety rebound or of a withdrawal syndrome. Moreover, the substitution with cyamemazine for 6 weeks is followed by a better withdrawal success rate after a considerable period of time (6 months).

The cyamemazine can be prepared according to American Patent 2877224.

As pharmaceutically acceptable salts of cyamemazine, mention may be made in particular of the addition salts with inorganic acids such as hydrochloride, sulphate, nitrate or phosphate, or with organic acids such as acetate, propionate, succinate, oxalate, benzoate, fumarate, maleate, methanesulphonate, isethionate, theophillineacetate, salicylate, phenolphthalinate or methylenebis-β-oxy-napthoate, or substitution derivatives of these derivatives.

The medicinal products consist of at least cyamemazine in free form or in the form of an addition salt with a pharmaceutically acceptable acid, in the pure state or in the form of a composition in which it is combined with any other pharmaceutically compatible product, which may be inert or physiologically active. The medicinal products according to the invention may be used orally, parenterally, rectally or topically.

As solid compositions for oral administration, use may be made of tablets, pills, powders (gelatin capsules, cachets) or granules. In these compositions, the active principle according to the invention is mixed with one or more inert diluents, such as starch, cellulose, sucrose, lactose or silica, under a stream of argon. These compositions may also comprise substances other than the diluents, for example one or more lubricants such as magnesium stearate or talc, a dye, a coating (dragees) or a varnish.

As liquid compositions for oral administration, use may be made of pharmaceutically acceptable solutions, suspensions, emulsions, syrups and elixirs containing inert diluents such as water, ethanol, glycerol, plant oils or liquid paraffin. These compositions may comprise substances other than the diluents, for example wetting products, sweeteners, thickeners, flavouring products or stabilizers.

The sterile compositions for parenteral administration may preferably be aqueous or nonaqueous solutions, suspensions or emulsions. Solvents or vehicles which may be used include water, propylene glycol, a polyethylene glycol, plant oils, in particular olive oil, injectable organic esters, for example ethyl oleate, or other suitable organic solvents. These compositions may also contain adjuvants, in particular wetting agents, isotonic agents, emulsifiers, dispersants and stabilizers. The sterilization may be carried out in several ways, for example by aseptic filtration, by incorporating sterilizing agents into the composition, by irradiation or by heating. The compositions may also be prepared in the form of sterile solid compositions which may be dissolved at the time of use in sterile water or any other injectable sterile medium The compositions for rectal administration are suppositories or rectal capsules which contain, besides the active product, excipients such as cocoa butter, semi-synthetic glycerides or polyethylene glycols.

The compositions for topical administration may be, for example, creams, lotions, eyedrops, mouthwashes, nasal drops or aerosols.

The doses depend on the desired effect, on the duration of the treatment and on the route of administration used; they are generally between 10 and 100 mg per day, and in particular 25 to 100 mg orally for an adult with single doses ranging from 10 to 20 mg of active substance.

In general, the physician will determine the suitable dose as a function of the age, of the weight and of all the other factors specific to the individual to be treated.

The following examples illustrate medicinal products according to the invention:

EXAMPLE A

Tablets containing a dose of 20 mg of active product and having the composition below are prepared according to the usual technique:

| | |
|---|---|
| Cyamemazine | 20 mg |
| Mannitol | 64 mg |
| Microcrystalline cellulose | 50 mg |
| Polyvidone excipient | 12 mg |
| Sodium carboxymethylstarch | 16 mg |
| Talc | 4 mg |
| Magnesium stearate | 2 mg |
| Anhydrous colloidal silica | 2 mg |
| Mixture of methylhydroxypropylcellulose, polyethylene glycol 6000 and titanium dioxide (72/3.5/24.5) qs for 1 finished film-coated tablet weighing 245 mg | |

EXAMPLE B

Gelatin capsules containing a dose of 20 mg of active product and having the composition below are prepared according to the usual technique:

| | |
|---|---|
| Cyamemazine | 20 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE C

An injectable solution containing 10 mg of active product and having the composition below is prepared:

| | |
|---|---|
| Cyamemazine | 10 mg |
| Benzoic acid | 80 mg |
| Benzyl alcohol | 0.06 $cm^3$ |
| Sodium benzoate | 80 mg |
| 95% ethanol | 0.4 $cm^3$ |
| Sodium hydroxide | 24 mg |
| Propylene glycol | 1.6 $cm^3$ |
| Water q.s. for | 4 $cm^3$ |

The invention also relates to the use of cyamemazine, or a pharmaceutically acceptable salt thereof, for preparing a medicinal product which can be used for abrupt benzodiazepine withdrawal by substitution of the benzodiazepine with cyamamazine.

The invention also relates to the method for preparing medicinal products which can be used in abrupt benzodiazepine withdrawal by substitution of the benzodiazepine with cyamemazine, consisting in mixing cyamemazine, or the pharmaceutically acceptable salts of this compound, with one or more compatible and pharmaceutically acceptable diluents and/or adjuvants.

The invention also relates to the method for treating abrupt benzodiazepine withdrawal, consisting in substituting, in the patient, benzodiazepine with cyamemazine or a pharmaceutically acceptable salt thereof.

More particularly, the treatment method consists in administering 10 to 100 mg per day of cyamemazine, taken as 1 to 3 doses, and more specially from 25 to 100 mg per day, as soon as the benzodiazepine is stopped.

I claim:

1. A method of treating benzodiazepine withdrawal, comprising: substituting for the benzodiazepine in a patient in need thereof, a benzodiazepine withdrawal symptom alleviating effective dose of cyamemazine, or a pharmaceutically acceptable salt thereof.

2. The method according to claim 1, wherein 10 milligrams to 100 milligrams per day of cyamemazine are substituted.

3. A method of treating benzodiazepine withdrawal, comprising: administering to a patient in need thereof, a benzodiazepine withdrawal symptom alleviating effective dose of cyamemazine, or a pharmaceutically acceptable salt thereof.

4. The method according to claim 3, wherein 10 to 100 mg per day of cyamemazine are administered.

* * * * *